(12) United States Patent
Yang et al.

(10) Patent No.: US 8,945,860 B2
(45) Date of Patent: Feb. 3, 2015

(54) HIGHLY SENSITIVE MONOCLONAL ANTIBODY RESIDUAL DETECTION ASSAY

(75) Inventors: Lihua Yang, Westborough, MA (US); Natarajan Ramasubramanyan, Westborough, MA (US)

(73) Assignee: Abbvie Inc., North Chicago, IL (US)

( * ) Notice: Subject to any disclaimer, the term of this patent is extended or adjusted under 35 U.S.C. 154(b) by 381 days.

(21) Appl. No.: 13/231,280

(22) Filed: Sep. 13, 2011

(65) Prior Publication Data

US 2012/0129196 A1    May 24, 2012

Related U.S. Application Data

(60) Provisional application No. 61/382,413, filed on Sep. 13, 2010.

(51) Int. Cl.
| | |
|---|---|
| G01N 33/53 | (2006.01) |
| G01N 33/566 | (2006.01) |
| G01N 33/563 | (2006.01) |
| C07K 16/42 | (2006.01) |
| G01N 33/68 | (2006.01) |

(52) U.S. Cl.
CPC .............. G01N 33/53 (2013.01); C07K 16/42 (2013.01); G01N 33/6854 (2013.01)
USPC ........... 435/7.92; 435/7.1; 436/501; 436/512; 530/389.3

(58) Field of Classification Search
None
See application file for complete search history.

(56) References Cited

U.S. PATENT DOCUMENTS

| | | | |
|---|---|---|---|
| 4,983,530 A * | 1/1991 | Carlson | 436/518 |
| 5,429,925 A | 7/1995 | Vanderlaan et al. | |
| 5,618,681 A | 4/1997 | Friedman et al. | |
| 2003/0054424 A1 | 3/2003 | Allen et al. | |
| 2008/0135490 A1 | 6/2008 | Li et al. | |

FOREIGN PATENT DOCUMENTS

| | | |
|---|---|---|
| EP | 1207393 | 5/2002 |
| WO | WO9320443 | 10/1993 |
| WO | WO2004029072 | 4/2004 |
| WO | WO2006086799 | 8/2006 |

OTHER PUBLICATIONS

Van Sommeren et al. "Comparison of three activated agaroses for use in affinity chromatography: Effects on coupling performance and ligand leakage" Journal of Chromatography A vol. 639, Issue 1, 4 Jun. 1993, pp. 23-31.*

Qin et al. "Point-of-Care Time-resolved Immunofluorometric Assay for Human Pregnancy-associated Plasma Protein A: Use in First-Trimester Screening for Down Syndrome" Clinical Chemistry 48:3 473-483 (2002).*

International Search Report and Written Opinion for PCT Application No. PCT/US2011/051356, dated Nov. 8, 2011.

* cited by examiner

*Primary Examiner* — Christine Foster
(74) *Attorney, Agent, or Firm* — Lathrop & Gage LLP; Andrew T. Wilkins; Peter W. Dini

(57) ABSTRACT

The present invention relates to compositions and highly sensitive methods for the detection of biotechnology product residual when monitoring product carry over and/or for cleaning verification in the manufacture of biotechnology products. In particular, the present invention is directed to immunoassays wherein one or more capture antibodies, or antigen binding fragments thereof, are used to detect residuals associated with the production of biotechnology products.

5 Claims, 10 Drawing Sheets

Figure 1:
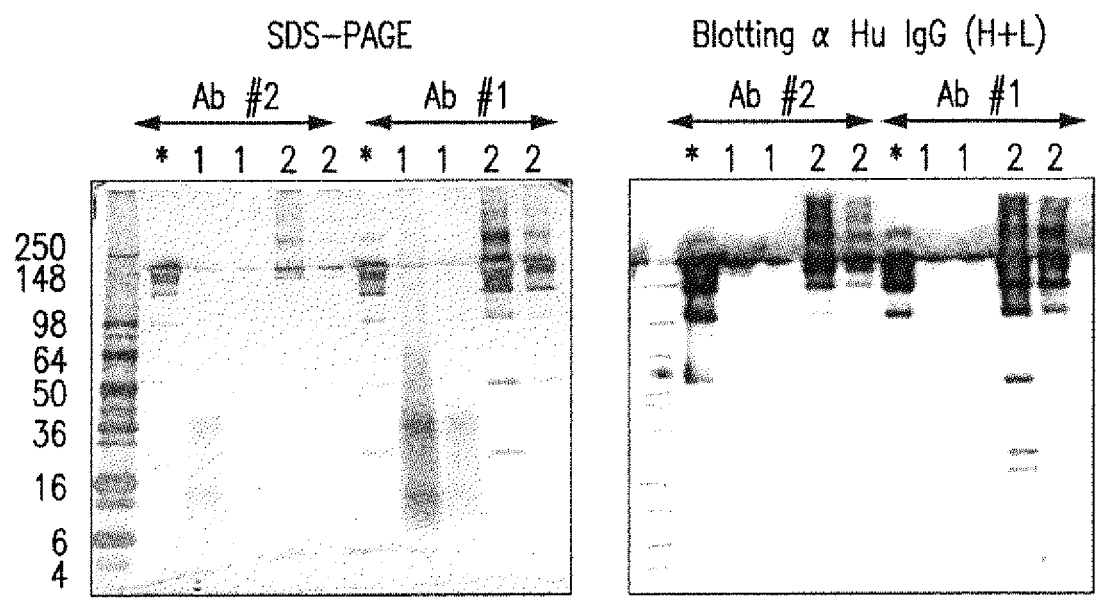

Lane 1: SeeBlue Plus2 STD
Lane 2: Blank
Lane 3: Ab #1
Lane 4: Ab #2
Lane 5: Ab #11
Lane 6: Ab #3
Lane 7: Ab #13
Lane 8: Ab #9
Lane 9: Blank
Lane 10: SeeBlue Plus2 STD

HIGHLY SENSITIVE MONOCLONAL ANTIBODY RESIDUAL DETECTION ASSAY

1. INTRODUCTION

The present invention relates to compositions and highly sensitive methods for the detection of biotechnology product residuals when monitoring product carry over and/or for cleaning verification in the manufacture of biotechnology products. In particular, the present invention is directed to immunoassays wherein one or more capture antibodies, or antigen binding fragments thereof, are used to detect residuals associated with the production of biotechnology products.

2. BACKGROUND OF THE INVENTION

Process equipment cleaning verification is required for Good Manufacturing Procedure ("GMP") compliance and such compliance is intended to ensure that therapeutic products meet the quality and purity characteristics that they purport, or are represented, to possess. As part of GMP compliance, the Total Organic Carbon ("TOC") assay has traditionally been used to verify the effectiveness of cleaning procedures for the removal of biotechnology product residuals. The TOC assay can be employed between individual production runs as well as when production sites are switched between distinct products. However, an important limitation of the TOC assay is that the detection limit, <0.1 ppm, may be unsuitable for monitoring product carry over and/or cleaning verification for very low dose products, such as certain antibody therapeutics, whose maximum allowable carry over limit is below the TOC detection limit.

In addition to issues concerning compliance with very low dose products, the International Conference On Harmonization Of Technical Requirements For Registration Of Pharmaceuticals For Human Use ("ICH") document ICH Q7A, adopted by the U.S. Food and Drug Administration in 2001, as well as Health Canada Guide-0028, both recommend the development of active pharmaceutical ingredient ("API")-specific assays for monitoring product carry over and/or cleaning verification. As the TOC assay is not API-specific, but rather measures total organic carbon regardless of the source, it does not comply with such recommendations.

In light of the inherent limitations to the TOC assay, a more sensitive, and API-specific, assay would be desirable as an alternative or supplementary method to detect biotechnology product residuals when monitoring product carry over and/or for cleaning verification. The instant invention meets that need by introducing a general analytical assay to detect trace amounts of nucleic acid or protein residuals, including monoclonal antibody residuals, which can be used for monitoring product carry over and/or for cleaning verification.

3. SUMMARY OF THE INVENTION

In certain embodiments, the instant invention is directed to methods for detecting a biotechnology product residual wherein a test sample is contacted to a substrate comprising a capture antibody, or antigen binding fragment thereof, and detection of an antibody-antigen complex is indicative of the presence of a biotechnology product residual.

In certain embodiments, the instant invention is directed to methods for detecting a biotechnology product residual wherein a test sample is contacted to a substrate comprising a capture antibody, or antigen binding fragment thereof, and detection of an antibody-antigen complex is indicative of the presence of a biotechnology product residual, wherein detection of the antibody-antigen complex is achieved via monitoring the binding of a labeled detection antibody capable of binding the antibody-antigen complex.

In certain embodiments, the instant invention is directed to methods for detecting a biotechnology product residual wherein a test sample is contacted to a substrate comprising a capture antibody, or antigen binding fragment thereof, and detection of an antibody-antigen complex is indicative of the presence of a biotechnology product residual, wherein the presence of the biotechnology product residual is indicative of product carry over.

In certain embodiments, the instant invention is directed to methods for detecting a biotechnology product residual wherein a test sample is contacted to a substrate comprising a capture antibody, or antigen binding fragment thereof, and detection of an antibody-antigen complex is indicative of the presence of a biotechnology product residual, wherein the presence of the biotechnology product residual is indicative of insufficient cleaning processes.

In certain embodiments, the instant invention is directed to methods for detecting a biotechnology product residual wherein a test sample is contacted to a substrate comprising a capture antibody, or antigen binding fragment thereof, and detection of an antibody-antigen complex is indicative of the presence of a biotechnology product residual, wherein the antigen is derived from a nucleic acid product.

In certain embodiments, the instant invention is directed to methods for detecting a biotechnology product residual wherein a test sample is contacted to a substrate comprising a capture antibody, or antigen binding fragment thereof, and detection of an antibody-antigen complex is indicative of the presence of a biotechnology product residual, wherein the antigen is a derived from an enzyme; a peptide hormone; a polyclonal antibody; a human monoclonal antibody; humanized monoclonal antibody; a chimeric monoclonal antibody; a single chain antibody; a Fab antibody fragment; a F(ab')2 antibody fragment; a Fd antibody fragment; a Fv antibody fragment; an isolated CDR; a diabody; and an immunoadhesion.

In certain embodiments, the instant invention is directed to methods for detecting a biotechnology product residual wherein a test sample is contacted to a substrate comprising a capture antibody, or antigen binding fragment thereof, and detection of an antibody-antigen complex is indicative of the presence of a biotechnology product residual, wherein the antigen is a derived from an antibody product.

In certain embodiments, the instant invention is directed to methods for detecting a biotechnology product residual wherein a test sample is contacted to a substrate comprising a capture antibody, or antigen binding fragment thereof, and detection of an antibody-antigen complex is indicative of the presence of a biotechnology product residual, wherein the capture antibody or antigen binding portion thereof, is selected from the group consisting of: anti-human IgG (H+L), anti-human IgG F(ab')2, anti-human IgG Kappa, anti-human IgG lambda, anti-mouse IgG (H+L) antibodies, and combinations thereof.

In certain embodiments, the instant invention is directed to methods for detecting a biological residue wherein a test sample is contacted to a substrate comprising two or more capture antibodies, or antigen binding fragments thereof, having distinct binding specificities, and where detection of an antibody-antigen complex is indicative of the presence of a biotechnology product residual the substrate comprises. In certain embodiments, the capture antibodies having distinct specificities will be present on the substrate in specific ratios.

4. BRIEF DESCRIPTION OF THE FIGURES

FIG. 1. depicts the results of experiments where selected detection antibodies (HRP conjugates) were tested for recognition of two products using SDS-PAGE and Western Blotting: Ab #1, the major target in this study, and Ab #2, as models to test recognition after exposure to the cleaning agents. Ab #1 and Ab #2 were incubated with CIP-100 (2.5%) and CIP-200 (2.5%) at 75° C. for 30 minutes to mimic stringent facility cleaning conditions. Following incubation, the test samples were neutralized. The intact molecules and neutralized treated samples were loaded onto SDS-PAGE and blotted against anti-human IgG (H+L). The figure specifically depicts SDS-PAGE and Western Blotting of anti-Human IgG (H+L) of Intact (*), CIP-100 treated (1) or CIP-200 treated (2) Ab #2 and Ab #1.

Figure 2:
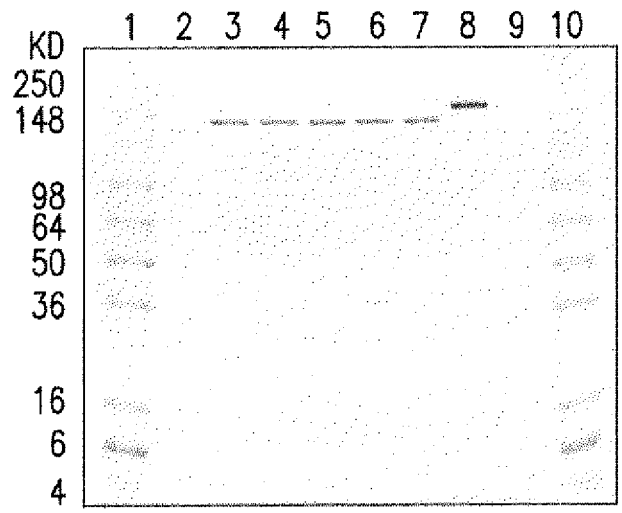

FIG. 2. depicts an SDS-PAGE separation of the following: SeeBlue Plus2 STD (Lane 1); Ab #1 (Lane 3); Ab #2 (Lane 4); Ab #11 (Lane 5); Ab #3 (Lane 6); Ab #13 (Lane 7); Ab #9 (Lane 8); and SeeBlue Plus2 STD (Lane 10). Lanes 3 and 9 are blanks.

Figure 3:
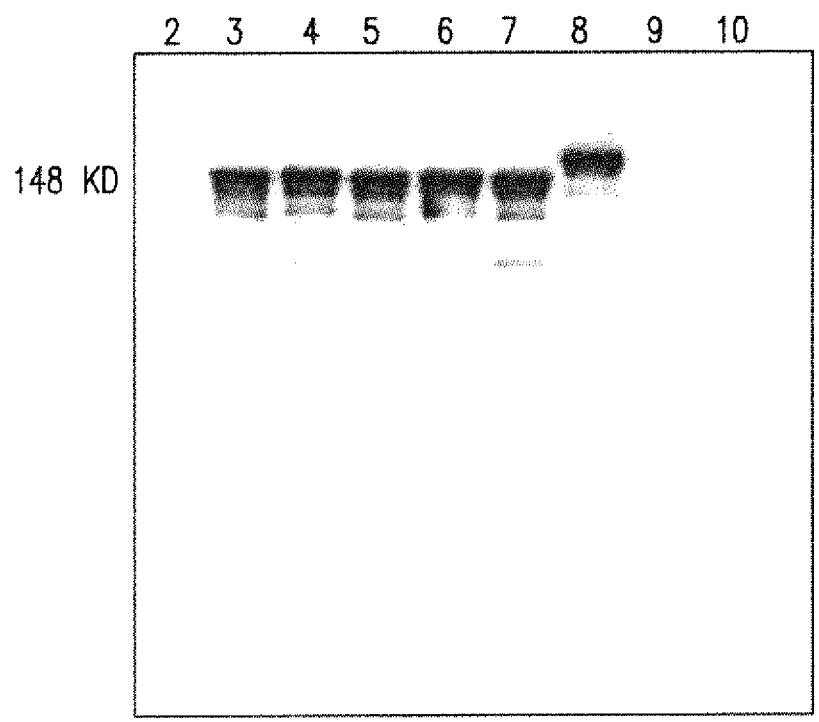

FIG. 3. depicts Western Blot analysis of an SDS-PAGE separation performed as outlined in FIG. 2, using Anti-Human IgG (H+L) antibody.

Figure 4:
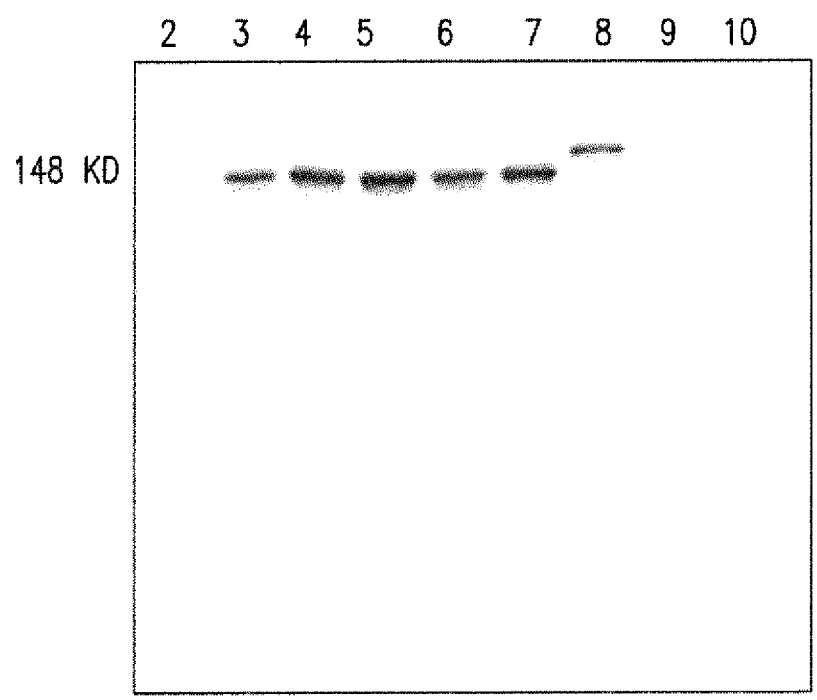

FIG. 4. depicts Western Blot analysis of an SDS-PAGE separation performed as outlined in FIG. 2, using Anti-Human IgG F(ab')2 antibody.

Figure 5:
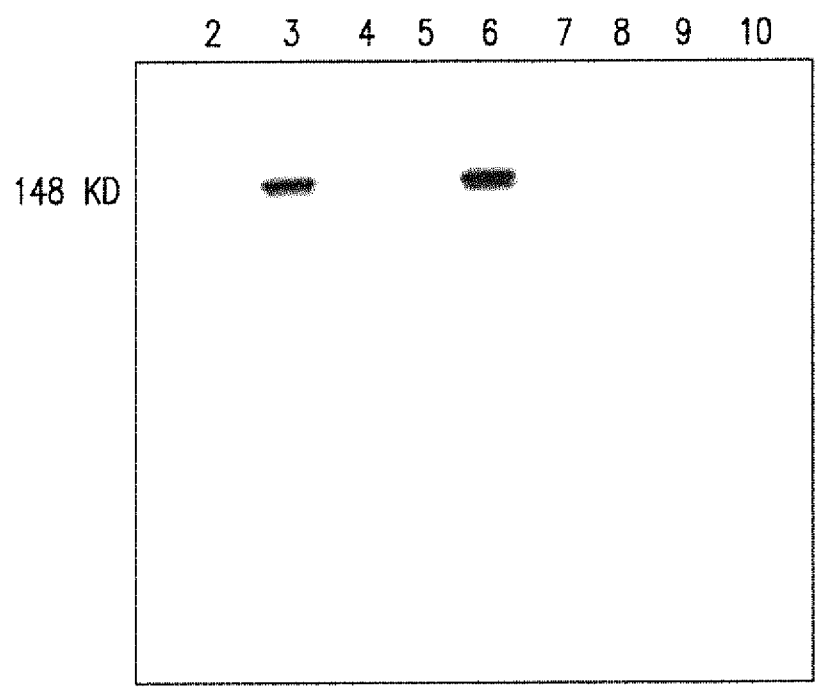

FIG. 5. depicts Western Blot analysis of an SDS-PAGE separation performed as outlined in FIG. 2, using Anti-Human IgG Lambda antibody.

Figure 6:
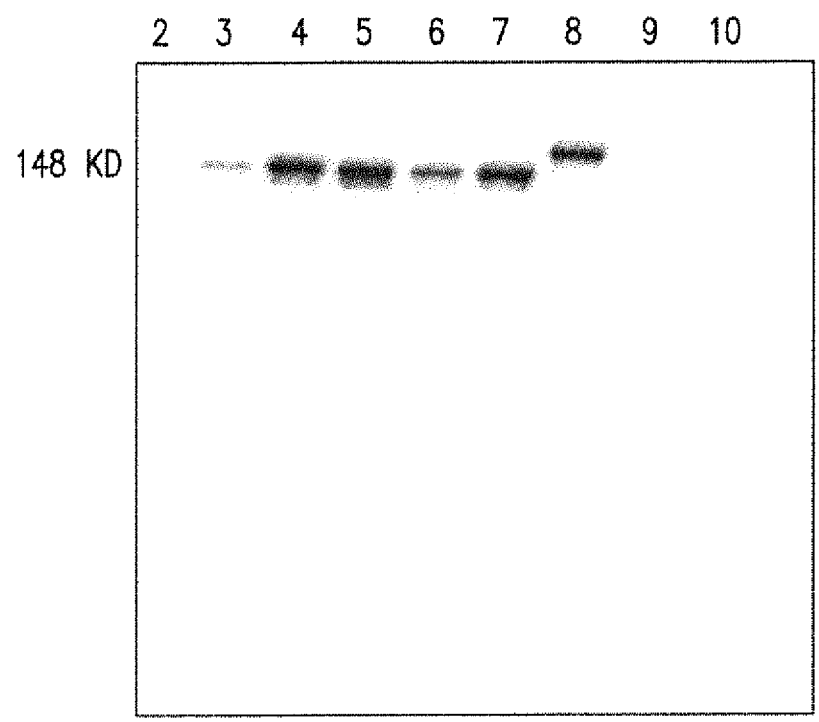

FIG. 6. depicts Western Blot analysis of an SDS-PAGE separation performed as outlined in FIG. 2, using Anti-Human IgG Kappa antibody.

Figure 7:
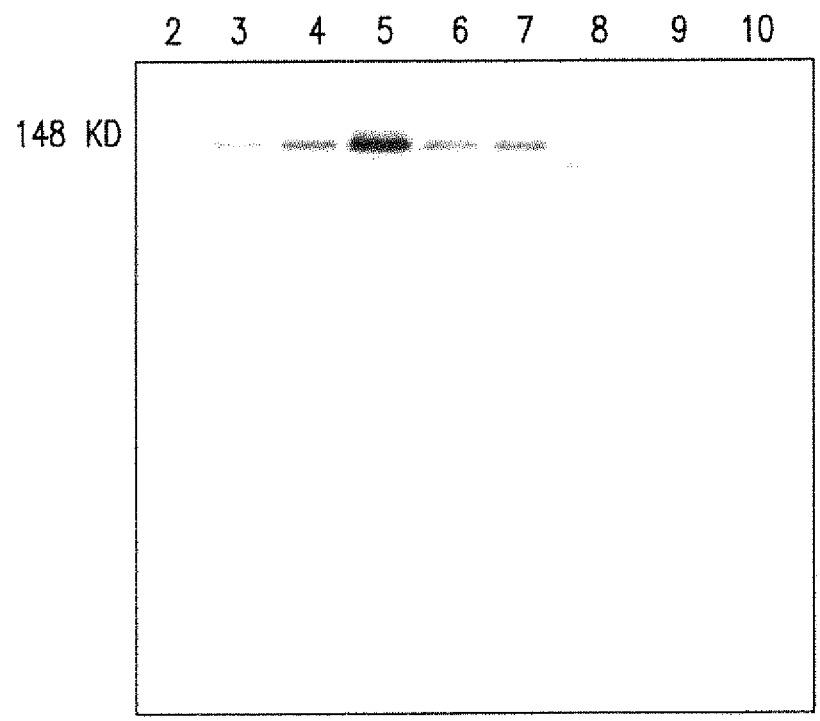

FIG. 7. depicts Western Blot analysis of an SDS-PAGE separation performed as outlined in FIG. 2, using Anti-Mouse IgG (H+L) antibody.

Figure 8:
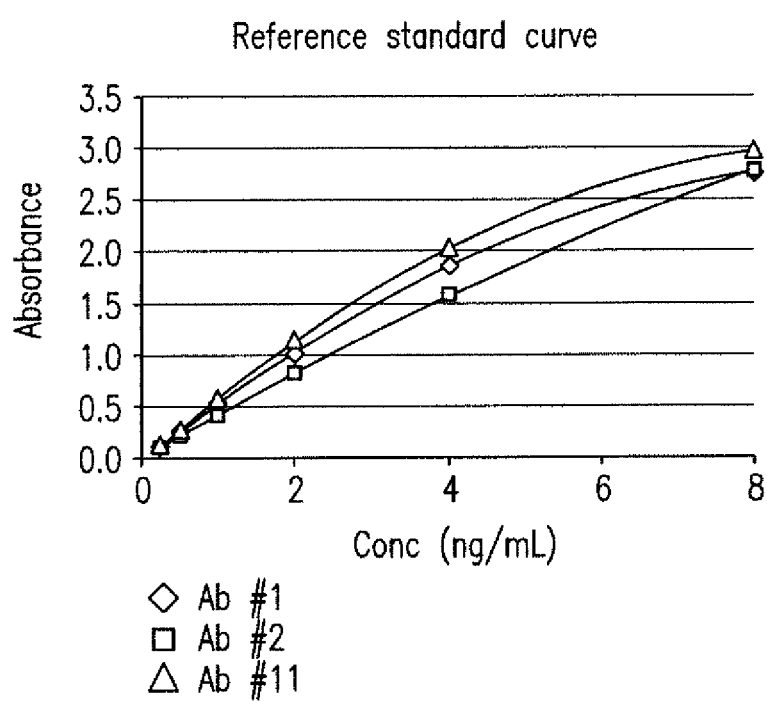

FIG. 8. depicts a reference standard curve based on the combined Abs (as outlined in Table 5, below), based on the combination's sensitivity and suitability for detection of Ab #1, Ab #2 and Ab #11. All the curves have a correlation coefficient of 0.9999 with a quadratic fit, and each curve range was 0.25 to 8 ng/mL.

Figure 9:
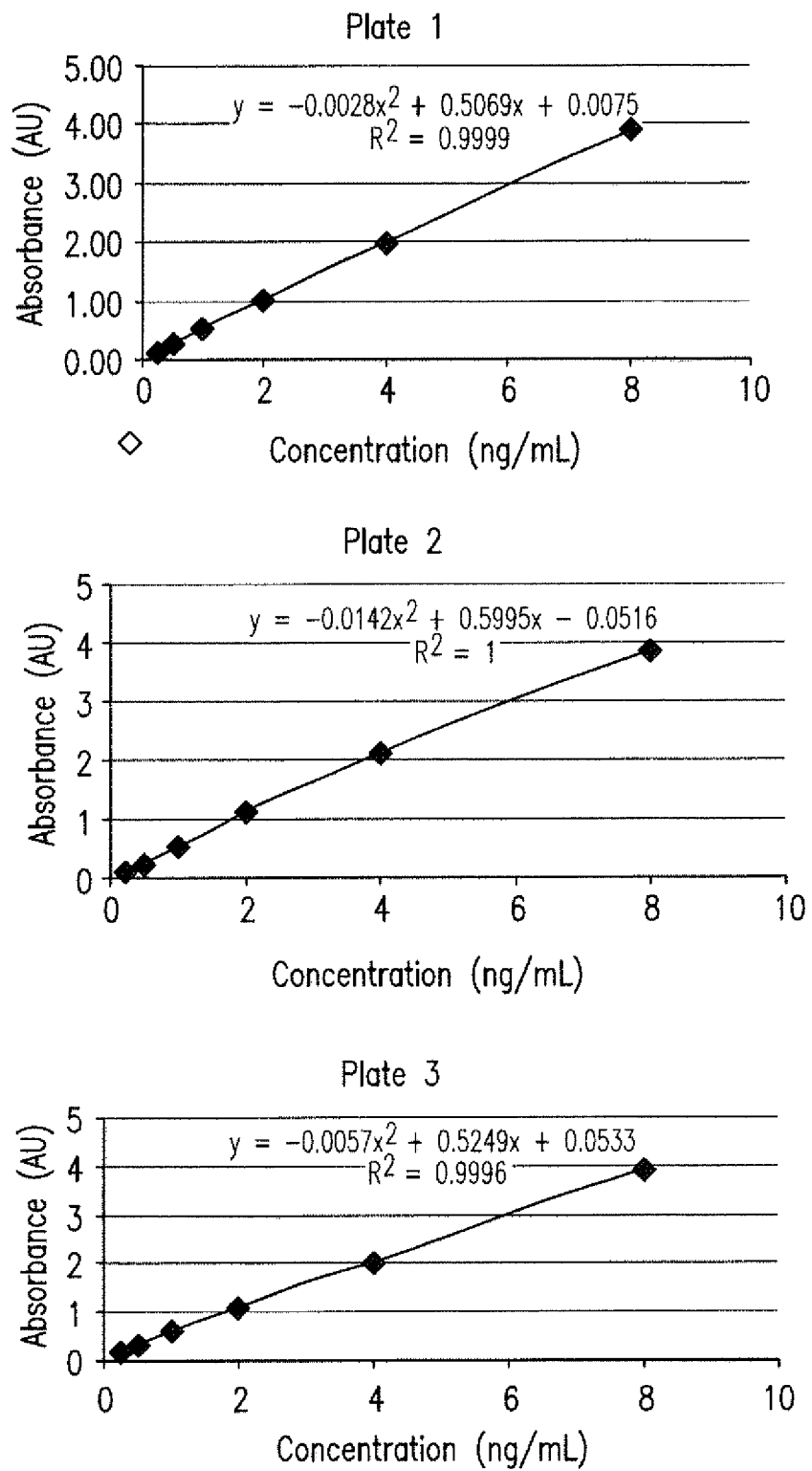

FIG. 9. depicts experiments directed to establishing the linearity of the analytical methods used herein. The "linearity" of an analytical method is its ability to elicit test results that are either directly, or by a well-defined mathematical transformation, proportional to the concentration of analyte of interest. The standards ranging from 0.25 to 8 ng/mL were prepared from Ab #1 drug substance. The standards and buffer blank were loaded on a plate and tested. The plot is shown in FIG. 9: Ab #1 Standard Curve (Plate 1, Top; Plate #2, Middle, and Plate #3, bottom). The correlation coefficient of the quadratic fit was greater than 0.999. The results indicate that the absorbance responses of the standards are proportional to the protein concentration by the quadratic fit.

Figure 10:
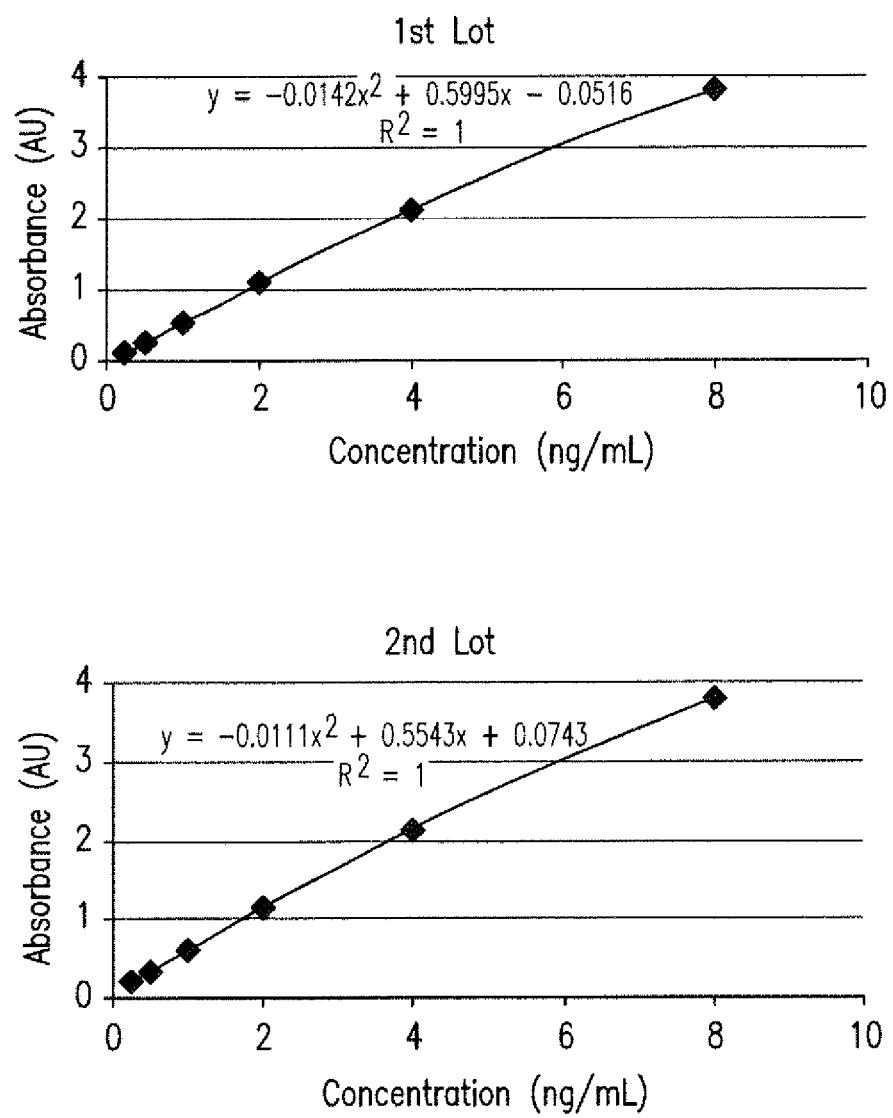

FIG. 10. depicts experiments directed to establishing the range of the analytical methods used herein. The "range" of an analytical method is the interval between the upper and lower levels of the analyte that can be determined with a suitable level of precision, accuracy and linearity using the method as written. The range of the assay was established as 0.25 to 8 ng/mL based on the linearity, accuracy, precision and quantitation limit. The correlation coefficient values of the quadratic fit was greater than 0.999. This indicates that in the range of 0.25 to 8 ng/mL, the absorbance responses are proportional to the protein concentration by the quadratic fit. The spike recovery studies were performed at 1.0, 2.0 and 4.0 ng/mL levels of standards in two different in-process samples. The recoveries were 100±7.9%. This indicates that the assay is precise and accurate in the estimated range. The results are summarized in Table 17 and the reference standard curves from the 1st and 2nd lots are displayed in FIG. 10: Ab #1 Standard Curve Using 1st (top) and 2nd (bottom) Lot Abs.

5. DETAILED DESCRIPTION OF THE INVENTION

The present invention relates to compositions and highly sensitive methods for the detection of biotechnology product residual when monitoring product carry over and/or for cleaning verification in the manufacture of such biotechnology products. In particular, the present invention is directed to immunoassays wherein one or more capture antibodies, or antigen binding fragments thereof, are used to detect residuals associated with the production of biotechnology products.

5.1 Carry Over Monitoring and Cleaning Verification

Carry over monitoring and cleaning verification via the compositions and methods of the instant invention can be directed to situations and process steps where contamination or carry over of materials poses the greatest risk to API quality. However, the compositions and methods of the instant invention are equally applicable to situations and process steps that pose minimal or no direct risk to API quality, but where use of the compositions and methods of the instant invention is otherwise desirable. Factors impacting the desirability of such implementations include, but are not limited to: employee health and safety, process equipment maintenance, the need for efficient process development optimization, as well as environmental conditions relating to the facilities and/or process equipment employed in the production of biotechnology products.

In certain embodiments, the monitoring of carry over and/or verification of cleaning procedures using the compositions and methods of the instant invention is designed to reflect actual equipment usage patterns. For example, but not by way of limitation, in circumstances where more than one API is manufactured using the same equipment and the equipment is cleaned by the same process, a representative API can be selected for validation via the compositions and methods of the instant invention. In alternative embodiments, a combination of one or more, or all, of the APIs manufactured using the same equipment can be selected for validation via the compositions and methods of the instant invention. In certain embodiments, the selection of the API, or combination of APIs, is based on factors such as, but not limited to, the solubility and difficulty of cleaning of the API. Furthermore, in certain embodiments, the calculation of residual limits will be based on factors such as, but not limited to, the potency, toxicity, and stability of the API.

In certain embodiments, the method of the instant invention involves sampling at particular process steps in order to monitor carry over and/or to verify cleaning procedures. In certain embodiments, sampling includes, but is not limited to, swabbing, rinsing, and any alternative method known to one of skill in the art for obtaining test material (e.g., direct extraction). In certain embodiments, sampling is performed to detect insoluble residuals. In alternative embodiments, sampling is employed to detect soluble residuals. In certain embodiments, sampling is employed to detect both insoluble and soluble residuals.

In certain embodiments the cleaning procedures are monitored at particular intervals after initial validation to ensure that the procedures remain effective when used during routine production. In certain embodiments, the interval will be after each production run. However, alternative intervals are known in the art, for example, but not limited to, after specific numbers of production runs, after particular process equipment, such as filters or vents, are replaced, or after specific production components, such as culture media, are introduced.

5.2 Biotechnology Product Residual Detection Assays

The present invention relates to biotechnology product residual detection assays comprising one or more capture antibodies, or antigen binding fragments thereof, capable of binding the product residual, or residuals, of interest. In certain embodiments, the capture antibody, or antigen binding fragment thereof, is employed in the context of an immunoassay. Such immunoassays include, but are not limited to, sandwich ELISAs, inhibition ELISAs, radioimmunoassays, florescence immunoassays, and chemiluminescent immunoassays. In a specific embodiment of the present invention, a sandwich ELISA is used.

In certain embodiments of the present invention, a sandwich ELISA is employed to assay a sample for biotechnology product residual(s). Generally speaking, in the sandwich ELISA, a surface is first prepared such that a quantity of capture antibody can be bound. Any nonspecific binding sites on the prepared surface are then blocked. Such blockage can be accomplished by methods known generally in the art, including, but not limited to, exposure of the surface to blocking proteins such as, but not limited to, bovine serum albumin. After blockage of nonspecific binding sites, the surface is contacted with a test sample. The surface is incubated with the test sample to allow for binding between product residuals and the capture antibody, should any product residual be present. Once the incubation period is complete, the surface is washed to remove unbound molecules. In certain embodiments, a second unlabeled antibody capable of binding the product residual is then added. In such embodiments, a third, enzyme-linked, or otherwise labeled, antibody specific to the constant region of the second antibody is added. The surface is then washed so that unbound antibody-label conjugates are washed away. A chemical is then added to trigger a signal from the label, e.g., a color or an electrochemical signal that can be measured. The signal is measured as an indication of the presence and quantity of target fragments. In alternative embodiments the second antibody is itself labeled or linked to an enzyme, thereby mooting the need for a third antibody.

In certain embodiments, the solid phase used as the surface on which the immunoasssay is performed can be any inert support or carrier that is essentially water insoluble, including supports/carriers in the form of surfaces, particles, porous matrices or the like. Exemplary supports/carriers include small sheets, Sephadex™, polyvinyl chloride, plastic beads, and assay plates or test tubes manufactured from polyethylene, polypropylene, polystyrene, and the like, including 96-well microtiter plates, as well as particulate materials such as filter paper, agarose, cross-linked dextran, and other polysaccharides. Alternatively, reactive water-insoluble matrices such as cyanogen bromide-activated carbohydrates and reactive substrates can be suitably employed for capture reagent immobilization.

In specific embodiments, the immobilized capture antibody is coated on a microtiter plate. For example, and not by way of limitation, the solid phase can be a multi-well microtiter plate, which can be used to analyze several samples at one time. Examples of microtiter plates include 96-well Elisa plates, such as Maxisorb™ or Immulon™ (Nunc, Roskilde, Denmark). Additionally, multiplex ELISA technologies, such as the Luminex™ technology may be employed to run hundreds of ELISAs simultaneously (Millipore). Such multiplex ELISA assay techniques are well known in the art and include, in addition to the Luminex™ technology, a variety of technologies that involve the use of multiple capture and/or detection antibodies for interrogating numerous analytes simultaneously. Discrimination among the various detection antibodies in such multiplex assays involves the use of multiple, distinct labels. Alternative multiplex assays technologies include the LiquiChip™ system (Qiagen) and the BD™ Cytometric Bead Array (BD Bioscience).

The present invention encompasses all capture antibodies exhibiting the required characteristics described herein. For example, but not by way of limitation, antibodies having the patterns of reactivity illustrated herein are within the scope of the invention regardless of the immunoglobulin class or subclass to which they belong. In particular embodiments suitable monoclonal antibodies can be of class IgG1, IgG2a, IgG2b, IgG3, or of classes IgM, IgA, or of any other known Ig classes or subclasses.

The selected capture antibodies or antigen binding fragments thereof of the present invention are immobilized on a suitable substrate by any method available to one of skill in the art. In certain embodiments the antibody or antigen binding fragment is linked directly to a selected functional group on the substrate. Alternatively, the antibody or antigen binding fragment is linked indirectly to the substrate via a linker or spacer. In certain non-limiting embodiments, linkage can be achieved by covalently attaching the capture antibody or antigen binding fragment thereof to streptavidin (or biotin) and then attachment to the substrate occurs indirectly via a biotin (or streptavidin) moiety that is covalently linked to the substrate. Alternatively, a thiol-terminal silane can be used for coating of the substrate surface, and a heterobifunctional crosslinker, e.g., N-gamma-maleimidobutyryloxy succinimide ester (GMBS). can be used for antibody or antigen binding fragment attachment. See U.S. Pat. No. 5,077,210. With this method, the antibody or antigen binding fragment thereof can be immobilized at a high density (e.g., 2 ng/mm2).

Another type of surface immobilization technique uses polymer hydrogel matrices. These materials typically contain a large amount of water, are soft, and are bioinert. Examples include cross-linked polymer films of poly(vinyl alcohol) and films of carboxymethyldextran. See Kobayashi, J. and Y. Ikada, "Covalent Immobilization of Proteins Onto the Surface of Poly(vinyl alcohol) Hydrogel," Biomaterials, 12, (1991), pages 747-751; Johnsson, B. et al, "Immobilization of Proteins to a Carboxymethyldextran-Modified Gold Surface for Biospecific Interaction Analysis in Surface Plasmon Resonance Sensors," Anal. Biochem., 196, (1991), 268-277; Lofas, S. and B. Johnsson, "A Novel Hydrogel Matrix on Gold Surfaces in Surface Plasmon Resonance Sensors for Fast and Efficient Covalent Immobilization of Ligands," J. Chem. Soc. Commun., (1990), pages 1526-1528).

Capture antibodies of the present invention include, but are not limited to the following: α Hu IgG (H+L); α Hu IgG F(ab')2; α Hu IgG λ; α Hu IgG κ; and α Ms IgG (H+L).

In addition, the function provided by the capture antibody or antigen binding fragment thereof, e.g., binding particular biotechnology product residuals to the substrate surface, can be accomplished using alternatives to traditional monoclonal antibodies. Alternatives to traditional monoclonal antibodies include antibody mimetics, such as, but not limited to, affibodies, domain antibodies, nanobodies and unibodies.

In certain embodiments, multiple capture antibodies, or antigen binding fragments thereof, having distinct binding specificities are bound to the substrate surface. The inclusion of multiple capture antibodies, or antigen binding fragments thereof, allows for the detection of multiple biotechnology product residuals simultaneously. Such biotechnology product residuals can be derived from the same or different products. For example, but not by way of limitation, the production of a single monoclonal antibody product can result in a variety of product residuals including, but not limited to, heavy chain residuals, light chain residuals, variable region residuals, and constant regions residuals. In certain embodiments, the various capture antibodies, or antigen binding fragments thereof, will be present in specific ratios. One non-limiting example such a mixture of capture antibodies is outlined in Table 5, below, where the following antibodies: α Hu IgG (H+L); α Hu IgG F(ab')2; α Hu IgG λ; α Hu κ; and a Ms IgG (H+L) are present in the following ratio: 1:2:16:8:8.

After immobilization of a selected capture antibody, or antigen binding fragment thereof, onto a suitable substrate, and exposure of that capture antibody, or antigen binding fragment thereof, to a sample for monitoring of carry over and/or for cleaning verification, it is necessary to visualize binding of the biotechnology product residual. Such visualization is commonly accomplished via the addition of a detection antibody that specifically binds an epitope on the biotechnology product residual.

Detection antibodies may be detected directly through moieties such as fluorochrome, chemiluminescent, and radioactive labels, or indirectly through moieties, such as enzymes, that must be reacted or derivatized. Examples of moieties that can be detected directly include radioisotopes, fluorophores such as rare earth chelates or fluorescein and its derivatives; rhodamine and its derivatives. Examples of moieties that must be reacted or derivatized include, but are not limited to dansyl; umbelliferone; luciferases; luciferin, 2,3-dihydrophthalazinediones; horseradish peroxidase; alkaline phosphatase; b-galactosidase; glucoamylase; lysozyme; saccharide oxidases; heterocyclic oxidases; biotin/avidin; biotin/streptavidin; biotin/streptavidin-HRP; spin labels; bacteriophage labels; stable free radicals; and the like. Conventional methods are available to bind these detectable moieties covalently to a detection antibody. For example, coupling agents such as dialdehydes, carbodiimides, dimaleimides, bis-imidates, bis-diazotized benxidine, and the like may be used to tag the antibodies with the above-described labels.

Because the two antibodies in a sandwich assay operate most effectively when they each bind the target antigen but do not interact or bind to each other, the immobilized capture antibody, or antigen binding fragment thereof is tested for reactivity with the detection antibody, or in the case of a three antibody system, the secondary and detection antibodies. A low reactivity is preferred between the capture antibody or antigen binding fragment thereof and the detection antibody while retaining high affinity for the target antigen. Furthermore, antibody pairs will operate most effectively when they each bind the target biotechnology product residual at distinct locations. Accordingly, antibodies should be evaluated to avoid pairing those with overlapping binding specificities.

The use of capture antibodies or antigen binding fragments thereof against biotechnology product residuals is an advantageous approach for monitoring carry over and/or to validate cleaning. Because of the high specificity and sensitivity of monoclonal antibodies, the compositions and methods of the instant invention are able to detect very low dose biotechnology product residuals far below the current limits of the TOC assay. In addition, such antibody detection methods are capable of specifically identifying the presence of the API, or APIs, of interest and thus fall within the recommendations of the ICH Q7A and Health Canada Guide-0028.

5.3 Carry Over Monitoring and Cleaning Verification of Antibody Production

In certain embodiments, the instant invention is directed to compositions and methods for the monitoring product carry over and/or for cleaning verification in the context of the production of pharmaceuticals where the API is an antibody. In certain embodiments, the antibody may be employed in the context of the pharmaceutical as a naked antibody, as an antibody conjugated to a partner molecule (such as, but not limited to, a toxin or a label), or may be otherwise modified (such as, but not limited to, by inclusion of modified amino acids or by the addition, deletion, or modification of carbohydrate side chains). In certain embodiments, such monitoring of product carry over and/or cleaning verification will be in the context of the production of polyclonal antibodies. In certain embodiments such monitoring of product carry over and/or cleaning verification will be in the context of the production of monoclonal antibodies. In certain embodiments such monitoring of product carry over and/or cleaning verification will be in the context of the production of antibodies for use in research or diagnostic use. In certain embodiments, such monitoring of product carry over and/or cleaning verification will be in the context of the production of antibodies for therapeutic use.

In certain embodiments monitoring of product carry over and/or cleaning verification will be in the context of the production of monoclonal antibodies for therapeutic uses. There are three broad categories of therapeutic monoclonal antibody molecules currently in commercial production: fully human, humanized and chimeric antibodies. A fully human antibody molecule is an antibody derived from human cells or from non-human cells that express human immunoglobulin genes. In contrast, a humanized antibody is an antibody generated in non-human animal, such as a mouse, but which has been subsequently modified to reflect human antibody sequences. This modification occurs primarily to minimize immunological responses to administration of the antibody. However, in certain embodiments, humanized antibodies will retain one or more of the original non-human sequences. Such retention of non-human sequences is commonly performed in order to preserve the antibody's therapeutically effective activity. Finally, a chimeric antibody molecule is composed of the humanized constant region and non-human variable region. Chimeric antibodies are commonly produced using recombinant DNA technology to operably link the variable (antigen binding) region of an antibody produced in a non-human animal to the constant (immune system effector) region of a human antibody.

In certain embodiments, the instant invention is directed to compositions and methods for the monitoring product carry over and/or for cleaning verification in the context of fully human antibody production. In alternative embodiments, the instant invention is directed to compositions and methods for the monitoring product carry over and/or for cleaning verification in the context of humanized antibody production. In alternative embodiments, the instant invention is directed to compositions and methods for the monitoring product carry over and/or for cleaning verification in the context of chimeric antibody production. In certain embodiments, specifically embodiments where multiple antibodies are being produced using the same facilities and/or process equipment, the instant invention is directed to compositions and methods for the monitoring product carry over and/or for cleaning verification in the context of: fully human and humanized; fully human and chimeric; humanized and chimeric; or fully human, humanized, and chimeric antibody production.

Additional diversity among antibodies, including, but not limited to, therapeutic antibodies occurs in connection with the specific heavy and light chains that comprise a particular antibody. Immunoglobulin molecules are comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. For example, human antibodies can be divided into the following specific isotypes based on the amino acid sequence of their heavy chains: $IgA_1$, $IgA_2$, IgD, IgE, $IgG_1$, $IgG_2$, $IgG_3$, $IgG_4$, and IgM. In addition, antibodies can be divided into two groups depending on whether the sequence of their light chain is a kappa (κ) or lambda (λ) light chain sequence.

In certain embodiments, the instant invention is directed to compositions and methods for the monitoring product carry over and/or for cleaning verification in the context of $IgA_1$, $IgA_2$, IgD, IgE, $IgG_1$, $IgG_2$, $IgG_3$, $IgG_4$, and IgM antibody production. In alternative embodiments, the instant invention is directed to compositions and methods for the monitoring product carry over and/or for cleaning verification in the context of kappa or lambda antibody production. In certain embodiments, specifically embodiments where multiple antibodies are being produced using the same facilities and/or process equipment, the instant invention is directed to compositions and methods for the monitoring product carry over and/or for cleaning verification in the context of production of antibodies having any combination of antibody isotype and light chain usage.

In addition to full length antibodies, specific antibody fragments are often employed in research, development, and as therapeutics. For example, but not by way of limitation, such antibody fragments can comprise the entire antigen binding portion of the full length antibody or portions thereof. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other fauns of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques. In one aspect, the antigen binding portions are complete domains or pairs of complete domains.

In certain embodiments, the present invention includes compositions and methods for the detection of one or more, or any combination of, the antibody fragments and antibody fragment-containing molecules selected from the following, non-limiting, group: Fab; F(ab')2; Fd; Fv; scFv; isolated CDR(s); diabodies; and immunoadhesions.

5.4 Production of Capture and Detection Antibodies

The terms "capture antibody" and "detection antibody", as used in this section, refers to an intact antibody or an antigen binding fragment thereof. The capture and detection antibodies of the present disclosure can be generated by a variety of techniques, including immunization of an animal with the antigen of interest followed by conventional monoclonal antibody methodologies e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

One preferred animal system for preparing hybridomas is the murine system. Hybridoma production is a very well-established procedure. Immunization protocols and techniques for isolation of immunized splenocytes for fusion are known in the art. Fusion partners (e.g., murine myeloma cells) and fusion procedures are also known.

An antibody preferably can be a human, a chimeric, or a humanized antibody. Chimeric or humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In certain embodiments, the present invention involves the evaluation of a panel of capture and/or detection antibodies or antigen binding fragments thereof to identify the appropriate capture and/or detection antibody or antigen binding fragment thereof for the particular biotechnology product being produced. An exemplary, but non-limiting, panel includes: anti-human IgG (H+L), anti-human IgG F(ab')2, anti-human IgG Kappa, anti-human IgG lambda and anti-mouse IgG (H+L) antibodies. Anti-human IgG (H+L) are employed to capture and/or detect entire (fully human/humanized antibodies) product molecules; anti-human IgG F(ab')2, anti-human IgG kappa and anti-human IgG lambda will capture and/or detect the product binding sites if such binding sites are human or humanized; and anti-mouse IgG (H+L) will provide specificity for chimeric products. In certain embodiments, particularly those embodiments occurring after equipment cleaning, when the residual products may be fragmented, degraded or otherwise denatured, a combination of various capture and/or detection antibodies will ensure detection of as many product residuals as possible.

6. EXAMPLES

6.1. ELISA Detection Assay

The present invention is directed, in certain embodiments, to immunoassays wherein one or more capture antibodies, or binding fragments thereof, are used to detect residuals associated with the production of biotechnology products. As shown in Table 1, five commercially available capture antibodies were evaluated in connection with the initial assay development. These same five antibodies ("Ab") conjugated with horse radish peroxidase (HRP) were also evaluated in this study as detection antibodies.

TABLE 1

| Capture Antibody | | | |
|---|---|---|---|
| Ab specificity | Vendor | Capture Ab (cat#) | Detection Ab (cat#) |
| α Hu IgG (H + L) | Pierce | 31119 | 31412 |
| α Hu IgG F(ab')₂ | Pierce | 31122 | 31414 |
| α Hu IgGμ | Southern Biotech | 2070-01 | 2070-05 |
| α Hu IgGμ | Southern Biotech | 2060-01 | 2060-05 |
| α Ms IgG (H + L) | Pierce | 31164 | 31430 |

The selected detection antibodies (HRP conjugates) were tested for recognition of two products using Western Blotting: Ab #1, the major target in this study, and Ab #2, as models to test recognition after exposure to the cleaning agents. Ab #1 and Ab #2 were incubated with CIP-100 (2.5%) and CIP-200 (2.5%) at 75° C. for 30 minutes to mimic stringent facility cleaning conditions. Following incubation, the test samples were neutralized. The intact molecules and neutralized treated samples were loaded onto SDS-PAGE and blotted against anti-human IgG (H+L).

As shown in FIG. 1, the Ab #1 and Ab #2 residuals were detected by anti-human IgG (H+L). The CIP-100 treated samples were the most degraded. The degraded products were not detected, however the residual products were still detected. CIP-200 treated samples generated some aggregates and a significant amount of Ab residuals. The aggregates, and residual products were detected by anti-human IgG (H+L). Anti-human IgG (H+L) is suitable to detect monoclonal antibody products. The antibody concentration spiked into the cleaning solutions was anticipated to be approximately 1000 fold higher than an actual cleaning sample from a production changeover. The higher protein concentration was needed to select the ELISA detection reagents for assay development.

To further study the detection Ab recognition of general mAb molecules, fully human, humanized, chimeric, kappa and lambda light chain monoclonal antibodies, were tested against the five commercially available detection Abs in Table 1. The results are shown in FIG. 2 through FIG. 7.

All five detection Ab recognized the expected products (Table 2). Anti-human IgG (H+L) and anti-human IgG F(ab')2 recognized all products (FIG. 3 and FIG. 4). Anti-human IgG lambda only recognized Ab #1 and Ab #3 with lambda light chains (FIG. 5). Anti-human IgG kappa strongly recognized Ab #2, Ab #11, Ab #13 and Ab #9 with kappa light chains, but also had slight cross-reactivity with the other molecules (FIG. 6). Anti-mouse IgG (H+L) strongly recognized Ab #11, a mouse and human chimeric product, but also slightly detected other human products (FIG. 7). This slight cross-reactivity phenomenon was dose dependent in Western Blots since this method is not quantitative and no load quantity study was performed. Further studies to distinguish the cross-reactivity among the testing molecules is described below.

TABLE 2

| mAb Products Produced at ABC | | | |
|---|---|---|---|
| Molecule | Isotype | Species | Light chain |
| Ab #2 | IgG1 | Fully human | κ |
| Ab #3 | | | λ |
| Ab #4 (back up of Ab #3) | | Humanized | κ |
| Ab #5 | | | κ |
| Ab #6 | | | κ |
| Ab #7 | | | κ |
| Ab #8 (back up of Ab #7) | | | κ |
| Ab #9 (DVD, Ab #2 and Ab #14) | | | κ |
| Ab #10 (DVD AB #3 and AB #7) | | | κ |
| Ab #1 | | Humanized H, chimeric L (Hu and Rat) | λ |
| Ab #11 | | Chimeric | κ |
| Ab #12 | | Humanized | κ |
| Ab #13 | | | κ |

Each single capture and detection Ab was individually evaluated by the ELISA individually for the initial evaluation. The plate was coated with 10 μg/mL capture Ab and detected with 2 and 5 μg/mL detection Ab. Based on these screening results, each single Ab quantity was further studied by performing an experiment where each Ab was tested at three capture and six detection conditions against related products. Anti-human IgG (H+L) and IgG F(ab')2 were applied to Ab #1 since Ab #1 is the major target in the project. The conditions and experimental outcomes are shown in Table 3.

TABLE 3

Single Ab DOE and Results

| Antibody | Molecule | Capture Ab (μg/mL) | Detection Ab (μg/mL) | Curve range (ng/mL) | Lowest signal (AU) | Highest signal (AU) |
|---|---|---|---|---|---|---|
| α Hu IgG (H + L) | Ab #1 | 0.5 | 0.125 | 0.25-8.0 | 0.134 | 3.909 |
| | | | 0.25 | 0.125-4.0 | 0.124 | 3.135 |
| | | 1.0 | 0.25 | 0.25-8.0 | 0.182 | 3.873 |
| | | | 0.5 | 0.125-4.0 | 0.305* | 3.101 |
| | | 2.0 | 0.5 | 0.125-8.0 | 0.137 | 3.836 |
| | | | 1.0 | 0.125-2.0 | 0.207 | 3.756 |
| α Hu IgG F(ab')$_2$ | | 0.5 | 0.125 | 0.125-8.0 | 0.068 | 2.964 |
| | | | 0.25 | 0.125-8.0 | 0.340* | 3.902 |
| | | 1.0 | 0.25 | 0.25-8.0 | 0.105 | 3.918 |
| | | | 0.5 | 0.25-8.0 | 0.273 | 3.896 |
| | | 2.0 | 0.5 | 0.25-8.0 | 0.134 | 3.892 |
| | | | 1.0 | 0.125-4.0 | 0.132 | 3.177 |
| α Hu IgG Lambda | | 8.0 | 1 | 1.0-32 | 0.129 | 3.157 |
| | | | 4 | 0.25-8 | 0.105 | 3.789 |
| α Hu IgG Kappa | Ab #2 | 2.0 | 0.5 | 0.5-16 | 0.103 | 2.931 |
| | | | 1.0 | 0.25-8.0 | 0.199 | 2.861 |
| | | 4.0 | 1.0 | 0.25-16 | 0.117 | 3.374 |
| | | | 2.0 | 0.25-8.0 | 0.284 | 3.362 |
| | | 8.0 | 2.0 | 0.5-8.0 | 0.205 | 3.242 |
| | | | 4.0 | 0.5-8.0 | 1.344 | 3.179 |
| α Ms IgG (H + L) | Ab #11 | 1.0 | 0.25 | 2.0-64 | 0.162 | 2.372 |
| | | | 0.5 | 1.0-32 | 0.173 | 2.988 |
| | | 2.0 | 0.5 | 0.5-16 | 0.096 | 2.650 |
| | | | 1.0 | 0.5-16 | 0.179 | 3.255 |
| | | 4.0 | 1.0 | 0.5-16 | 0.172 | 3.227 |
| | | | 2.0 | 0.25-8.0 | 0.141 | 3.168 |

*Outlier, the plate well was contaminated and the values were not used for evaluation.

The goal of the single Ab testing was to find an optimal combination to achieve the best sensitivity for each Ab. The bolded conditions in Table 3 indicated that in the dynamic range of 0.25 to 8 ng/mL, the lowest signal was over 0.1, which is a reliable reading over background, and the highest signal reached the plate reader's maximum. Under those conditions, the assay reached over ten-fold sensitivity than Ab #1 required. Table 4 lists the Ab #1 allowable carry over limit.

TABLE 4

Ab #1 Requested Sensitivity

| Unit | Sampling | Sensitivity (ng/mL) |
|---|---|---|
| Overall Process | Swab | 4 |
| | Rinse | 7 |
| Upstream | Swab | 12 |
| | Rinse | 13 |
| Down stream | Swab | 8 |
| | Rinse | 7 |

$^a$ ELISA quantitation limit is 0.25 ng/mL.
$^b$ Dose dependent cross reactivity observed during western blotting screening was not observed in the ELISA, perhaps due to the lower concentration of sample tested (data not shown).

The five single Ab were combined according to the above-described experimental results, as shown in Table 5.

TABLE 5

Ab Combination

| Ab | Capture Ab (μg/mL) | Capture ratio | Detection Ab (μg/mL) | Probing ratio |
|---|---|---|---|---|
| α Hu IgG (H + L) | 0.5 | 1 | 0.125 | 1 |
| α Hu IgG F(ab')$_2$ | 1 | 2 | 0.25 | 2 |
| α Hu IgG λ | 8 | 16 | 4 | 32 |

TABLE 5-continued

Ab Combination

| Ab | Capture Ab (μg/mL) | Capture ratio | Detection Ab (μg/mL) | Probing ratio |
|---|---|---|---|---|
| α Hu κ | 4 | 8 | 1 | 8 |
| α Ms IgG (H + L) | 4 | 8 | 2 | 16 |

The combined Ab was re-confirmed for sensitivity and suitability for Ab #1, Ab #2 and Ab #11 detection. FIG. 8 displays the standard curve for those products. All the curves have a correlation coefficient of 0.9999 with a quadratic fit, and each curve range was 0.25 to 8 ng/mL.

The target for preparation of the coating and detection Ab pools was to be sufficient for 1000 plates. Based on the combination ratio, the large capture and detection Ab pools were prepared according to Table 6 and Table 7. The Ab pool was used for assay qualification.

TABLE 6

Capture Ab Pool

| Capture Ab | Stock conc (mg/mL) | Added Ab vol (µL) | Final vol (mL) | Final conc (µg/mL) | Pool Ab vol (µL) |
|---|---|---|---|---|---|
| α Hu IgG (H + L) | 1.8 | 2.22 | 8 | 0.5 | 566.7 |
| α Hu IgG F(ab')$_2$ | 2.4 | 3.33 | 8 | 1 | 850.0 |
| α Hu IgG λ | 1 | 64.0 | 8 | 8 | 16320.0 |
| α Hu IgG κ | 1 | 32.0 | 8 | 4 | 8160.0 |
| α Ms IgG (H + L) | 1.8 | 17.78 | 8 | 4 | 4533.3 |
| Total Ab vol (µL) | N/A | 119.3 | N/A | N/A | 30430.0 |
| One plate vol (µL) | | | 24 | | |
| Total plate numbers | | | 1275 | | |

TABLE 7

Detection Ab Pool

| Detection Ab | Stock conc (mg/mL) | Added Ab vol (µL) | Final vol (mL) | Final conc (µg/mL) | Pool Ab vol (µL) |
|---|---|---|---|---|---|
| α Hu IgG (H + L) | 0.8 | 1.25 | 8 | 0.125 | 400.0 |
| α Hu IgG F(ab')$_2$ | 0.8 | 2.50 | 8 | 0.25 | 800.0 |
| α Hu IgG λ | 1.0 | 32 | 8 | 4 | 10240.0 |
| α Hu IgG κ | 1.0 | 8 | 8 | 1 | 2560.0 |
| α Ms IgG (H + L) | 0.8 | 20 | 8 | 2 | 6400.0 |
| Total Ab | N/A | 63.8 | N/A | N/A | 20400.0 |
| One plate vol (µL) | | | 13 | | |
| Total plate numbers | | | 1600 | | |

To verify the reliability of the assay, SP eluate and final ultrafiltration/diafiltration ("UF/DF") from Ab #1 scale up run were employed for assay qualification. Those samples were reported to be approximately 5 mg/mL and were diluted accordingly for this study.

Under normal conditions, drug substance samples were stored at −80° C. prior to testing. Storage conditions at ambient temperature for 4 hours, 2°-8° C. for 48 hours and three freeze/thaw cycles were challenged to cover possible lab circumstances. The results are summarized in Table 8. The protein results were not affected significantly by different storage conditions (<10%).

TABLE 8

Effect of Sample Storage

| | Ab #1 Protein Conc (ng/mL) | |
|---|---|---|
| Sample storage conditions | SP eluate | UF/DF |
| −80° C. storage | 2.22 | 2.08 |
| Ambient temperature for 4 hours | 2.11 | 1.89 |
| 2-8° C. for 48 hours | 2.06 | 2.2 |
| Three freeze/thaw cycles | 2.06 | 1.88 |

The ELISA substrate color development time was set for 14 minutes. To assess the time variability, 14±1 minutes were tested. The results were not affected during a 1 minute window (Table 9).

TABLE 9

Substrate Development Time

| | Ab #1 Protein conc (ng/mg) | | |
|---|---|---|---|
| Sample | 13 mins | 14 mins | 15 mins |
| SP eluate | 2.12 | 2.06 | 2.06 |
| UF/DF | 2.16 | 2.02 | 2.08 |

Test plates were read immediately after addition of 2 M phosphoric acid to stop the reaction, and then read again after sitting in the ambient temperature for 30 minutes. There were no significant differences observed (<10%) (Table 10).

TABLE 10

Plate Incubation Time

| | Ab #1 Protein conc (ng/mg) | |
|---|---|---|
| Sample | Initial | 30 mins |
| SP eluate | 2.06 | 2.02 |
| UF/DF | 1.95 | 1.91 |

The "precision" of the analytical method is the degree of agreement among individual test results when the method is applied repeatedly to multiple samplings of a homogeneous sample.

"Assay repeatability" measures the precision of the analytical procedure when it is performed multiple times under uniform analytical conditions. Six aliquots of SP eluate and final UF/DF were tested within one plate. The protein concentration was calculated in each aliquot. The percent relative standard deviation of the concentration value was calculated using all six measurements. The results are summarized in Table 11. The relative standard deviations for the protein measurements were <7%.

TABLE 11

Assay Repeatability

| | Ab #1 Protein conc (ng/mL) | |
|---|---|---|
| Aliquot # | SP | UF/DF |
| 1 | 2.082 | 1.967 |
| 2 | 2.186 | 2.117 |
| 3 | 2.293 | 2.179 |
| 4 | 2.466 | 2.086 |
| 5 | 2.014 | 2.203 |
| 6 | 2.304 | 1.908 |
| Mean | 2.224 | 2.077 |
| Std Dev | 0.150 | 0.107 |
| % RSD | 6.75 | 5.15 |

"Intermediate precision" is a measurement of the scatter of test results produced within the laboratory when the analytical procedure is performed on different days or by different analysts.

Three aliquots each of SP eluate and final UF/DF were tested. This experiment was repeated two additional times on different days by a different analyst. The first three results from the assay repeatability part of study were used for the Day 1 of this study. Results are shown in Table 12. The percent relative standard deviation for the protein measurement was <5%, within the expected precision range of 20%.

TABLE 12

Intermediate Precision

| | | | Ab #1 Protein conc (ng/mL) | | | |
|---|---|---|---|---|---|---|
| Day | Analyst | Replicate# | SP eluate | Mean | UF/DF | Mean |
| 1 | 2 | 1 | 2.082 | 2.19 | 1.967 | 2.09 |
| | | 2 | 2.186 | | 2.117 | |
| | | 3 | 2.293 | | 2.179 | |
| 2 | 1 | 1 | 1.992 | 2.06 | 2.059 | 2.02 |
| | | 2 | 2.042 | | 1.999 | |
| | | 3 | 2.137 | | 2.009 | |
| 3 | 2 | 1 | 2.011 | 2.01 | 2.116 | 2.06 |
| | | 2 | 2.007 | | 2.074 | |
| | | 3 | 1.989 | | 1.979 | |
| Mean | | | 2.08 | 2.08 | 2.06 | 2.06 |
| Std Dev | | | 0.10 | 0.09 | 0.07 | 0.03 |
| % RSD | | | 4.97 | 4.48 | 3.53 | 1.59 |

To estimate the quantification limit, the lowest point of the standard curve, 2-fold serial dilutions of 8 ng/mL Ab #1 standards were prepared six times and loaded on six different plates. The results are shown in Table 13. According to ICH guidelines, the quantification limit of the assay is the minimum concentration at which signal to noise ratio is higher than 10:1 and relative standard deviation is less than 20%. The noise of the blank measurements was 0.004 AU. The average signal of the 0.25 ng/mL standard was 0.122 AU. While 0.125 ng/mL meets the criteria, 0.25 was chosen as the LOQ to ensure assay robustness. The quantitation limit was set at 0.25 ng/mL with the signal to noise ratio of 30.5:1 and relative standard deviation of 14%.

TABLE 13

Quantitation Limit Study

| Ab #1 standard | | | OD Values | | | | | | |
|---|---|---|---|---|---|---|---|---|---|
| conc (ng/mL) | Curve #1 | Curve #2 | Curve #3 | Curve #4 | Curve #5 | Curve #6 | Mean | STDEV | % RSD |
| 0.031 | 0.018 | 0.025 | 0.010 | 0.019 | 0.021 | 0.013 | 0.018 | 0.005 | 31 |
| 0.063 | 0.036 | 0.038 | 0.020 | 0.027 | 0.031 | 0.041 | 0.032 | 0.008 | 24 |
| 0.125 | 0.066 | 0.069 | 0.053 | 0.051 | 0.058 | 0.053 | 0.058 | 0.008 | 13 |
| 0.25 | 0.151 | 0.110 | 0.130 | 0.110 | 0.106 | 0.125 | 0.122 | 0.017 | 14 |
| 0.50 | 0.234 | 0.239 | 0.240 | 0.235 | 0.225 | 0.242 | 0.236 | 0.006 | 3 |
| 1.00 | 0.483 | 0.451 | 0.461 | 0.454 | 0.454 | 0.450 | 0.459 | 0.012 | 3 |
| 2.00 | 0.951 | 0.934 | 0.951 | 0.909 | 0.893 | 0.891 | 0.922 | 0.028 | 3 |
| 4.00 | 2.431 | 1.870 | 1.741 | 1.697 | 1.715 | 1.693 | 1.890 | 0.310 | 16 |
| 8.00 | 3.880 | 2.982 | 2.765 | 3.880 | 2.772 | 2.733 | 3.169 | 0.558 | 18 |

Noise = 0.004,
10X Noise = 0.04

The "linearity" of an analytical method is its ability to elicit test results that are either directly, or by a well-defined mathematical transformation, proportional to the concentration of analyte of interest.

The standards ranging from 0.25 to 8 ng/mL were prepared from Ab #1 drug substance. The standards and buffer blank were loaded on a plate and tested. The plot is shown in FIG. 9. The correlation coefficient of the quadratic fit was greater than 0.999. The results indicate that the absorbance responses of the standards are proportional to the protein concentration by the quadratic fit.

The accuracy of the assay was studied using the spike and recovery method. SP eluate and final UF/DF were spiked at final standard levels of 1.0, 2.0 and 4.0 ng/mL. The assay was calculated as the ratio of the concentration of the protein recovered divided by the experiment concentration of the spike and expressed as a percentage. The results of this study are shown in Table 14. Recoveries of the spikes were in the range of 100±7.9% for all spike levels.

TABLE 14

Spike and Recovery

| | A4 #1 Protein concentration (ng/mL) | | | | |
|---|---|---|---|---|---|
| Sample | Spike level (ng/mL) | Spike level (ng/mL) | Spiked sample | Experimental value of spiking solution | % Recovery |
| SP Eluate | 1 | 0.965 | 1.907 | 0.940 | 100.2 |
| | 2 | 0.954 | 2.901 | 2.021 | 96.3 |
| | 4 | 0.976 | 4.509 | 3.896 | 90.7 |
| UF/DF | 1 | 0.945 | 1.916 | 1.010 | 96.1 |
| | 2 | 0.952 | 2.920 | 2.077 | 94.8 |
| | 4 | 0.925 | 4.524 | 3.906 | 92.1 |

SP eluate and final UF/DF samples were serial diluted two-fold in the reference standard curve calibration range to evaluate the sample dilutional linearity. Shown in Table 15, the sample dilutions did not affect the results. The variable was less than 10%. Only three dilution points were needed to confirm the sample dilution for unknown sample testing.

TABLE 15

Sample Dilutional Linearity

| SP eluate (ng/mL) | | | UF/DF (ng/mL) | | |
|---|---|---|---|---|---|
| Response | Dilution Fold | Results | Response | Dilution Fold | Results |
| 6.278 | 1 | 6.278 | 8.022 | 1 | 8.022 |
| 3.363 | 2 | 6.726 | 4.146 | 2 | 8.292 |
| 1.679 | 4 | 6.716 | 2.202 | 4 | 8.808 |
| 0.804 | 8 | 6.432 | 1.027 | 8 | 8.216 |
| 0.356 | 16 | 5.696 | 0.484 | 16 | 7.744 |

TABLE 15-continued

Sample Dilutional Linearity

| | SP eluate (ng/mL) | | | UF/DF (ng/mL) | | |
|---|---|---|---|---|---|---|
| Response | Dilution Fold | Results | Response | Dilution Fold | Results |
| Mean | N/A | 6.37 | N/A | N/A | 8.22 |
| Std Dev | N/A | 0.42 | N/A | N/A | 0.39 |
| % CV | N/A | 6.63 | N/A | N/A | 4.78 |

The "range" of an analytical method is the interval between the upper and lower levels of the analyte that can be determined with a suitable level of precision, accuracy and linearity using the method as written. The range of the assay was established as 0.25 to 8 ng/mL based on the linearity, accuracy, precision and quantitation limit. The correlation coefficient values of the quadratic fit was greater than 0.999. This indicates that in the range of 0.25 to 8 ng/mL, the absorbance responses are proportional to the protein concentration by the quadratic fit. The spike recovery studies were performed at 1.0, 2.0 and 4.0 ng/mL levels of standards in two different in-process samples. The recoveries were 100±7.9%. This indicates that the assay is precise and accurate in the estimated range.

To cover the future needs of the commercial supplies, a second lot of each antibody was evaluated. Table 16 indicates the 1st lot which was used for large pool and the 2nd lot for comparison.

TABLE 16

Ab Lots Used for Results Comparison

| Ab | Vendor | Capture 1sr Lot | Capture 2$^{nd}$ Lot | Detection 1$^{st}$ Lot | Detection 2$^{nd}$ Lot |
|---|---|---|---|---|---|
| α Hu IgG (H + L) | Pierce | JL1176621 | JG1151545 | JL1181032, 1 | JG1151545 |
| α Hu IgG F(ab')$_2$ | Pierce | JL1179911 | JK1177611 | JK1176627, 1 | JI1165881 |
| α Hu IgG λ | Southern Biotech | D1908-M509 D1908-M409 | D1908-WL38 | G8902-YE27D, 11 | G8902-YE27B |
| α Hu IgG κ | Southern Biotech | A5007-M399 | A5007-ZA98 | C5406-P687C, 3 | A5007-PP28B |
| α Ms IgG (H + L) | Pierce | JK1177612 | LA1185962 | JJ127078, 4 | JJ127078 |

The results are summarized in Table 17 and the reference standard curves from the 1st and 2nd lots are displayed in FIG. 10. The 2nd lot did not affect the outcome.

TABLE 17

Second Lot Ab Comparison

| | Protein conc (ng/mL) | |
|---|---|---|
| Sample | 1$^{st}$ Lot | 2$^{nd}$ Lot |
| SP eluate | 2.10 | 2.01 |
| UF/DF | 2.08 | 2.06 |

To evaluate the assay suitability for the detection of residual product protein levels in the equipment rinsates, the recovery of protein from equipment surfaces was studied. The production equipment was made of stainless steel, hastalloy or glass. A representative coupon (i.e., a representative sample such as a swab, a rinsate, or other sample form) of each of the material was spotted with 40 mL of Ab #1 drug substance, which was diluted to 2 and 3 ppm. The surface was allowed to air dry for 3 to 4 hours, and then rinsed with 40 mL of MilliQ water. The rinsates were collected. The protein recovery off the surface was calculated as the ratio of the concentration of the protein in the rinsate divided by concentration of spike and expressed as percentage.

As shown in Table 18, the average recovery is 76% for glass surface, 87% for stainless steel and 76% for hastalloy. The results met the passing criteria (50-150%) and demonstrated that the assay is suitable for production equipment rinsing sample testing.

TABLE 18

Surface Rinsing Recovery

| Study concentration | | 2 ppm | | | 3 ppm | | |
|---|---|---|---|---|---|---|---|
| Surface material | Rep# | Spiked level (ng/mL) | Rinsate level (ng/mL) | Recovery (%) | Spiked level (ng/mL) | Rinsate level (ng/mL) | Recovery (%) |
| Glass | 1 | 3.15 | 2.18 | 69 | 5.37 | 4.05 | 75 |
| | 2 | | 2.08 | 66 | | 4.59 | 85 |
| | 3 | | 2.17 | 69 | | 4.79 | 89 |
| | Avg Recovery (%) | | | 76 | | | |
| Stainless steel | 1 | 3.15 | *6.48 | N/A | 5.37 | 4.80 | 90 |
| | 2 | | 2.39 | 76 | | 5.03 | 94 |
| | 3 | | 2.68 | 85 | | 4.84 | 90 |
| | Avg Recovery (%) | | | 87 | | | |
| Hastalloy | 1 | 3.15 | 2.35 | 75 | 5.37 | 4.26 | 79 |
| | 2 | | 2.01 | 64 | | 4.55 | 85 |

TABLE 18-continued

Surface Rinsing Recovery

| | | 2 ppm | | | 3 ppm | | |
|---|---|---|---|---|---|---|---|
| Study concentration Surface material | Rep# | Spiked level (ng/mL) | Rinsate level (ng/mL) | Recovery (%) | Spiked level (ng/mL) | Rinsate level (ng/mL) | Recovery (%) |
| | 3 | | 1.90 | 60 | | 5.03 | 94 |
| | Avg Recovery (%) | | | 76 | | | |

The Ab #1 process validation includes blank runs after the product process run to evaluate the product carryover. The blank runs include Protein A, SP sepharose and Q Sepharose chromatography, and UF/DF operations. The product A to A carryover will be evaluated using Bradford assay, however, the residual carryover limit (RCL) for product A to B is 4 ng/mL (VR-2249, VR-2250 and VR-2251) which is below the Bradford assay LOQ (1.25 ug/mL). The mAb assay was evaluated for its suitability to support Ab #1 A to B carryover study. The process buffer interference with the assay was evaluated by performing the buffer spike and recovery experiments. Each of the process buffers at neat and five fold dilution (with ample dilution buffer) were spiked at final standard levels of 1.0, 2.0 and 4.0 ng/mL.

As shown in Table 19, the recovery is approximately 70% for Q Sepharose elution buffer SR-488 and SP Sepharose eluation buffer SR-610 which was within the pass criteria (50 to 150%), but Protein A elution buffer SR-493 only recovered 1.1% due to acidic conditions which interfere with the antigen and antibody binding.

TABLE 19

Spike and Recovery for Neat Ab #1 Process Buffers

| | | Ab #1 Protein concentration (ng/mL) | | | | |
|---|---|---|---|---|---|---|
| Unit operation | Buffer | Spike level (ng/mL) | Experimental value of spiking solution | Spiked sample | % Recovery | Average recovery |
| Q Sepharose | SR-488, pH 7.4 | 1 | 0.958 | 0.669 | 69.8 | 68.0 |
| | | 2 | 1.745 | 1.096 | 62.8 | |
| | | 4 | 3.21 | 2.291 | 71.4 | |
| SP Sepharose | SR-610, pH 6.9 | 1 | 0.958 | 0.632 | 66 | 70.3 |
| | | 2 | 1.745 | 1.245 | 71.3 | |
| | | 4 | 3.21 | 2.364 | 73.6 | |
| Protein A | Protein SR-493, pH 3.5 | 1 | 1.087 | 0.017 | 1.6 | 1.1 |
| | | 2 | 2.174 | 0.021 | 1 | |
| | | 4 | 4.179 | 0.03 | 0.7 | |

The spike and recovery results of diluted buffer are summarized in Table 20. The protein recovery was acceptable from 110.3 to 121.9% when diluted five fold. The assay quantitation limit is 1.25 ng/mL with five fold dilution. Therefore, for a robust assay operation, a five fold dilution is recommended for all three process buffers. This assay format with an LOQ of 1.25 ng/mL is suitable to assess product A to B carryover.

TABLE 20

Spike and Recovery for Five Fold Diluted Ab #1 Process Buffers

| | | Ab #1 Protein concentration (ng/mL) | | | | |
|---|---|---|---|---|---|---|
| Unit operation | Buffer | Spike level (ng/mL) | Experimental value of spiking solution | Spiked sample | % Recovery | Average recovery |
| Q Sepharose | SR-488, pH 7.4 | 1 | 0.958 | 1.154 | 120.5 | 110.3 |
| | | 2 | 1.745 | 1.827 | 104.7 | |
| | | 4 | 3.21 | 3.399 | 105.9 | |
| SP Sepharose | SR-610, pH 6.9 | 1 | 1.087 | 1.34 | 123.3 | 121.9 |
| | | 2 | 2.174 | 2.608 | 120.0 | |
| | | 4 | 4.179 | 5.12 | 122.5 | |
| Protein A | Protein SR-493, pH 3.5 | 1 | 1.087 | 1.287 | 118.4 | 117.7 |
| | | 2 | 2.174 | 2.535 | 116.6 | |
| | | 4 | 4.179 | 4.936 | 118.1 | |

A new assay format and conditions to detect general residual mAb related products have been developed. The above-described results demonstrate the reproducibility of the assay. The new assay is capable of quantifying trace levels of mAb proteins with a quantitation limit of 0.25 ng/mL for Ab #1. Thus, the newly developed mAb ELISA provides a valuable tool for quantifying the residual mAb related molecules for facility changeover and cleaning verifications.

The performance of the assay for Ab #1 product quantification in in-process samples was qualified. The assay robustness, precision, quantification limit, linearity, accuracy, sample dilutional linearity, range, 2nd lot commercial reagents were studied. All the above results are within the expected accuracy and precision for an ELISA. Assay conditions are summarized in Table 21. In addition, the recovery study proved that this assay is suitable for rinsate studies and Ab #1 process carryover studies. However, for blank runs, a five fold dilution is needed to eliminate the buffer interference.

TABLE 21

Assay Conditions

| | |
|---|---|
| Coating Ab quantity | 24 µL cocktail Ab |
| Coating incubation | overnight at 4° C. |
| Blocking | Casein in PBS, 60 mins at 37° C. |
| Plate wash cycles | 5 cycles |
| Sample incubation | 60 mins at 37° C. |
| Detection Ab quantity | 12.8 µL cocktail Ab |
| Detection Ab incubation | 60 mins at 37° C. |
| K-blue substrate development | 14 mins at RT |

The above-described assay was used to test final rinses from the cleaning cycles performed on the bioreactor, harvest and downstream process tanks, flex hoses and filter housings which contained Antibody #1 process intermediates after GMP-1. The final rinses were all below LOQ. In addition, the intermediate rinses were sampled for bioreactor Z-3200 and tank TK-2830. As shown in Table 23, only the first USP water rinses from Z-3200 and TK-2830 detected protein residuals at very low level. The results further proved the above-described assay's sensitivity and specificity.

TABLE 23

Cleaning Results for Equipment Rinsate for GMP-1*

| Type of equipment | Sample ID | TRX4 residual level |
|---|---|---|
| hoses | final rinse | <LOQ |
|  | negative control | <LOQ |
| filter housing | F-8190-2, final rinse | <LOQ |
|  | F-8190-3, final rinse | <LOQ |
|  | F-8190-3, negative control | <LOQ |
| Bioreactor | 1st rinse—initial USF water rinse | 1.86 µg/mL |
|  | 2nd rinse—hot USP water rinse after CIP-100 | <LOQ |
|  | 3nd rinse—hot USP wate rinse after CIP-200 | <LOQ |
|  | 4th rinse—WFI rinse | <LOQ |
|  | 5th rinse—Final WFI rinse | <LOQ |
| Harvest tank | final rinse | <LOQ |
| 200 L process tank | final rinse | <LOQ |
| 700 L process tank | final rinse | <LOQ |
| Filter bases | F-8190 final rinse | <LOQ |
| 1100 L TK-2830 | 1st rinse—initial USP water rinse | 0.54 µg/mL |
|  | 2st rinse—hot USP water rinse after CIP-100 | <LOQ |
|  | 3rd rinse—hot USP water rinse after CIP-200 | <LOQ |
|  | 4th rinse—WFI rinse | <LOQ |
|  | 5th rinse—WFI rinse | <LOQ |
|  | 6th rinse—WFI rinse | <LOQ |
|  | final rinse—Final WFI rinse | <LOQ |
| ¾ inch flex hoses | final rinse | <LOQ |

*LOQ = 0.25 ng/mL.

The final rising samples from the equipment associated with the process validation runs were tested by the above-described assay. All the samples tested were below LOQ. The results from the process validation run 1 ("PV-1") are listed in Table 24. After cleaning, the reportable Antibody #1 level (0.25 ng/ml) is at least 16 fold below the maximum allowable carryover limit (4-13 ng/mL).

TABLE 24

Cleaning Results for Equipment Rinsate for PV-1

| Description | ELISA Result |
|---|---|
| Chrom Skid Z-2340 | <LOQ |
| Bioreactor Z-3200 | <LOQ |
| Z-3200 Harvest Transfer Line | <LOQ |
| Filter Bases F-8190-4, F-8190-1, F-7665, F-7666 | <LOQ |
| F-7665 Dome | <LOQ |
| F-7666 Dome | <LOQ |
| F-8190-1 Dome (or F-8190-4) | <LOQ |
| Harvest Tank TK-3210 | <LOQ |
| TK-3210 Product Transfer Line | <LOQ |
| 1100 L Surge Tank TK-2060 | <LOQ |
| 200 L Process Tank TK-4170 | <LOQ |
| 1.5 inch flexhoses | <LOQ |
| 700 L Capture Chrom Eluate Pooled Tank TK-2665 | <LOQ |
| 1100 L SP Seph Load Tank TK-2830 | <LOQ |
| 200 L SP Seph Eluate Tank TK-2138 | <LOQ |
| Chrom Skid Z-2330 | <LOQ |
| 200 L Q Seph Load Tank TK-3224 | <LOQ |
| UF Skid Z-2815 | <LOQ |
| 200 L Q Seph FTW Tank TK-3226 | <LOQ |
| 900 L Viral Filtrate Tank TK-2845 | <LOQ |
| Flowmeter FI-7565 | <LOQ |
| ¾ inch flexhoses | <LOQ |
| Valve 1½ inch | <LOQ |
| Valve ¾ inch | <LOQ |
| Valve 1 inch | <LOQ |
| Ported Valve 1½ × 1 inch | <LOQ |
| Tee with Valve 1½ × ½ inch | <LOQ |
| Tee 1½ × ¾ inch | <LOQ |
| Tee 1½ × 1½ inch | <LOQ |
| Tee ¾ × ¾ inch | <LOQ |
| Tee 1 × 1 inch | <LOQ |
| Tee 1½ × 1 inch | <LOQ |
| Elbow 1/1½ inch | <LOQ |
| Reducer 2 × 1½ inch | <LOQ |
| Reducer 1 × ¾ inch | <LOQ |
| Sight Glass 1/1½ inch | <LOQ |
| Gasket 2 inch | <LOQ |
| Clamp 2 inch | <LOQ |
| Top Plate 12 inch housing | <LOQ |
| Bottom Plate 12 inch housing | <LOQ |
| Follower Tube 12 inch housing | <LOQ |
| Seal Nut 12 inch housing | <LOQ |
| Compression Spring 12 inch housing | <LOQ |
| Center Post 12 inch housing | <LOQ |
| O-ring 1½ inch 12 | <LOQ |
| O-ring ¾ inch | <LOQ |
| Top Plate 18 inch housing | <LOQ |
| Bottom Plate 18 inch housing | <LOQ |
| Follower Tube 18 inch housing | <LOQ |
| Seal Nut 18 inch housing | <LOQ |
| Compression Spring 18 inch housing | <LOQ |
| Center Post 18 inch housing | <LOQ |
| Large Bin | <LOQ |
| Large Bin Lid | <LOQ |
| Small Bin | <LOQ |
| Small Bin Lid | <LOQ |
| Cross 1 inch | <LOQ |
| Reducer 1½ × 1 inch | <LOQ |
| Spool Piece 1 inch × 5.2 inch | <LOQ |
| Spool Piece 1 inch × 17.4 inch | <LOQ |
| Valve 1 × ½ inch | <LOQ |
| F-7282 Dome | <LOQ |
| F-7282 Base | <LOQ |
| Dip Tube—1½ in DT-2060 | <LOQ |
| Dip Tube—¾ inch DT-9238 | <LOQ |
| Dip Tube—1 inch DT-3224 | <LOQ |
| 1 × 1 × 1½ inch Instrument Tee | <LOQ |
| 1 inch Elbow | <LOQ |
| 1 inch sight glass | <LOQ |

Due to the high assay sensitivity, the mAb products routinely worked with in the lab could potentially cause contamination in this assay. Therefore, it is recommended that precautions are taken to ensure that the equipment and environment used during the sample testing is as clean as possible.

Various publications are cited herein, the contents of which are hereby incorporated in their entireties.

What is claimed is:

1. A method for detecting an antibody product, or fragment thereof, the method comprising:
    (a) contacting a test sample suspected of containing the antibody product or fragment thereof with a substrate comprising a mixture of five or more distinct classes of capture antibodies or antigen binding fragments thereof so as to form at least one capture antibody-antibody product complex;
    wherein the five or more distinct classes of capture antibodies or antigen binding fragments thereof are: anti-human IgG heavy and light chains (H+L), anti-human IgG F(ab')$_2$, anti-human IgG lambda, anti-human IgG kappa, and anti-mouse IgG (H+L) antibodies; and wherein the anti-human IgG (H+L), anti-human IgG F(ab')$_2$, anti-human IgG lambda, anti-human IgG kappa, and anti-mouse IgG (H+L) antibodies are present in the mixture in a ratio of 1:2:16:8:8;

(b) detecting the at least one capture antibody-antibody product complex using a composition capable of detecting the at least one capture antibody-antibody product complex, wherein detection of the at least one capture antibody-antibody product antigen-complex is indicative of the presence of the antibody product, or fragment thereof, in the test sample.

2. The method of claim 1, wherein the composition capable of detecting the at least one capture antibody-antibody product complex is a labeled detection antibody capable of binding the at least one capture antibody-antibody product antigen complex.

3. The method of claim 1, wherein the presence of antibody product, or fragment thereof, is indicative of product carry over.

4. The method of claim 1, wherein an amount of the antibody product, or fragment thereof, is indicative of an effectiveness of a cleaning process.

5. The method of claim 1, wherein the antibody product or fragment thereof is selected from the group consisting of: polyclonal antibodies; human monoclonal antibodies; humanized monoclonal antibodies; chimeric monoclonal antibodies; single chain antibodies; Fab antibody fragments; F(ab')$_2$ antibody fragments; Fd antibody fragments; Fv antibody fragments; and diabodies.

* * * * *